United States Patent
Ekchian et al.

(10) Patent No.: US 10,696,769 B2
(45) Date of Patent: Jun. 30, 2020

(54) PH-SENSITIVE POLYMERIC COMPOSITIONS, KITS, AND METHODS

(71) Applicant: Massachusetts Institute of Technology, Cambridge, MA (US)

(72) Inventors: Gregory James Ekchian, Belmont, MA (US); Michael John Cima, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 75 days.

(21) Appl. No.: 15/366,740

(22) Filed: Dec. 1, 2016

(65) Prior Publication Data

US 2017/0152334 A1    Jun. 1, 2017

Related U.S. Application Data

(60) Provisional application No. 62/261,365, filed on Dec. 1, 2015.

(51) Int. Cl.
| | |
|---|---|
| *C08F 220/34* | (2006.01) |
| *C08F 220/06* | (2006.01) |
| *G01N 33/84* | (2006.01) |
| *A61B 5/1468* | (2006.01) |
| *A61B 5/00* | (2006.01) |
| *C08L 33/14* | (2006.01) |
| *A61B 5/145* | (2006.01) |

(52) U.S. Cl.
CPC .......... *C08F 220/34* (2013.01); *A61B 5/1468* (2013.01); *A61B 5/14539* (2013.01); *A61B 5/4848* (2013.01); *C08F 220/06* (2013.01); *C08L 33/14* (2013.01); *G01N 33/84* (2013.01); *A61B 5/14507* (2013.01); *C08F 2800/20* (2013.01)

(58) Field of Classification Search
CPC .. C08F 220/34; C08F 220/06; C08F 2800/20; G01N 33/84
See application file for complete search history.

(56) References Cited

U.S. PATENT DOCUMENTS

| | | | |
|---|---|---|---|
| 4,906,717 A | 3/1990 | Cretenot et al. | |
| 6,307,372 B1 | 10/2001 | Sugarman et al. | |
| 6,751,491 B2 | 6/2004 | Lew et al. | |
| 2004/0248326 A1* | 12/2004 | Ziaie | A61K 9/0024 438/1 |
| 2013/0233093 A1* | 9/2013 | Pohl | G01N 1/10 73/863.21 |

FOREIGN PATENT DOCUMENTS

| | | |
|---|---|---|
| EP | 1647283 A1 | 4/2006 |
| EP | 1716870 A1 | 11/2006 |
| WO | 00/47111 A1 | 8/2000 |
| WO | 2015/0055727 A1 | 4/2015 |

OTHER PUBLICATIONS

Cordeiro et al., "Synthesis of Well-Defined Poly(2-(dimethylamino)ethyl methacrylate) under Mild Conditions and Its Co-Polymers with Cholesterol and PEG using Fe(0)/Cu(II) based SARA ATRP," Polym. Chem., 2013, 4:3088-3097.
Kodibagkar et al., "Novel 1H NMR Approach to Quantitative Tissue Oximetry Using Hexamethyldisiloxane," Magnetic Resonance in Medicine, 2006, 55:743-748.
Liu et al., "Biodegradation of Cellulose by β-Glucosidase and Cellulase Immobilized on a pH-Responsive Copolymer," Biotechnology and Bioprocess Engineering, 2014, 19(5):829-837.
Liu, V. "Magnetic Resonance Imaging Contrast Agents for Chemical Sensing," Massachusetts Institute of Technology, Doctoral Thesis, Jun. 2014, pp. 125-141.
Vassiliou, C. C. "Biopsy-Implanatable Chemical Sensor," Massachusetts Institute of Technology, Doctoral Thesis, Sep. 2013.
Vassiliou, C.C. et al. "Miniaturized, biopsy-implantable chemical sensor with wireless, magnetic resonance readout," Lab Chip, 2015, 15, 3465-3472.
International Search Report, PCT/US2016/064420, dated Feb. 27, 2017.

* cited by examiner

*Primary Examiner* — Robert D Harlan
(74) *Attorney, Agent, or Firm* — Eversheds Sutherland (US) LLP (57) ABSTRACT

Provided herein are polymeric compositions having a relaxation time that is a function of pH. The polymeric compositions can include an anionic monomer, a cationic monomer, and a crosslinker. The crosslinker may comprise at least one of a diacrylate crosslinker and a dimethacrylate crosslinker. Also provided herein are methods of pH sensing, and methods of forming a polymeric composition. Kits of parts also are provided that include a polymeric composition. The polymeric compositions may be used to determine the pH of one or more biological tissues and/or liquids.

32 Claims, 2 Drawing Sheets

PH-SENSITIVE POLYMERIC COMPOSITIONS, KITS, AND METHODS

CROSS-REFERENCE TO RELATED APPLICATIONS

This application claims priority to U.S. Provisional Patent Application No. 62/261,365, filed Dec. 1, 2015, which is incorporated herein by reference.

GOVERNMENT LICENSE RIGHTS

This invention was made with government support under grant number 5-U54-CA151884 awarded by the National Institutes of Health. The government has certain rights in the invention.

BACKGROUND

Several pH-sensitive hydrogels are known, such as those that include poly-hydroxyethylmethacrylate (p-HEMA) crosslinked with N,N'-methylenebisacrylamide (BIS). p-HEMA-BIS hydrogels have been used as sensors, because the transverse relaxation time ($T_2$) of the p-HEMA-BIS hydrogels can depend on the pH of the environments in which the hydrogels are disposed.

Plots of the pH versus the $T_2$ relaxation time of the p-HEMA-BIS hydrogels, however, have revealed that the relaxation time may peak at about pH 6.5. The peak, therefore, occurs within several preferred detection ranges, including detection ranges that are physiologically relevant.

As a result, a single $T_2$ relaxation time can correspond to two, non-peak pH values, thereby imparting ambiguity to the results provided by the p-HEMA-BIS hydrogels. For example, if a $T_2$ relaxation time of about 200 ms corresponds to the peak pH of about 6.5, then a $T_2$ relaxation time of about 150 ms may correspond to an off-peak pH of about 6 and an off-peak pH of about 7.5.

There remains a need for a pH-sensitive polymeric compositions having relaxation times that correspond to a single pH value within preferred detection ranges.

BRIEF SUMMARY

Provided herein are polymeric compositions having a relaxation time that is a function of pH. In one embodiment, the relaxation time of the polymeric composition is unique at each pH within a range of about 4.5 to about 8. The polymeric compositions may comprise a crosslinked co-polymer comprising a cationic monomer, an anionic monomer, and a crosslinker. The mol ratio of the cationic monomer to the anionic monomer may be about 75:25 to about 25:75. The cationic monomer may comprise a side chain having a tertiary amine, and the anionic monomer may comprise a side chain having a carboxylic acid. The crosslinker may comprise at least one of a diacrylate crosslinker and a dimethacrylate crosslinker.

Also provided herein are methods of pH sensing. The methods may comprise associating a polymeric composition as provided herein with one or more biological tissues, one or more biological liquids, or a combination thereof, measuring a relaxation time of the polymeric composition, and determining a pH of the one or more biological tissues, one or more biological liquids, or a combination thereof by comparing the relaxation time of the polymeric composition with a standard curve comprising a plot and/or table of at least two known pH values and at least two previously measured relaxation times of the polymeric composition at the at least two known pH values.

Kits of parts also are provided, which may comprise a polymeric composition as provided herein, and a standard curve comprising a plot and/or table of at least two known pH values and at least two previously measured relaxation times of the polymeric composition at the at least two known pH values.

Also provided are methods of forming a polymeric composition. The methods may comprise providing a mixture comprising an anionic monomer, a cationic monomer, and a crosslinker, contacting the mixture with at least one initiator to form a polymerizable composition, and curing the polymerizable composition to form the polymeric composition. In one embodiment, the mol ratio of the cationic monomer to the anionic monomer in the mixture is about 75:25 to about 25:75. The crosslinker may be present in the mixture at a concentration of about 0.01 to about 10% by weight, based on the total weight of the anionic monomer, the cationic monomer, and the crosslinker, or, alternatively, about 0.01 to about 10 mol %, based on the total amount of cationic and anionic monomer.

Also provided herein are compositions comprising a first polymeric composition comprising a first crosslinked co-polymer comprising a first cationic monomer, a first anionic monomer, and a first crosslinker. The first polymeric composition may have a relaxation time that is a function of pH, and the relaxation time may be unique at each pH within a range of about 4.5 to about 8. The compositions may further include at least one of [1] a second polymeric composition and [2] at least one additional pH sensitive material. The first polymeric composition, the second polymeric composition, and the at least one additional pH sensitive material may have maximum relaxation times that occur at different pH values, compared to one another.

DETAILED DESCRIPTION

Provided herein are pH-sensitive polymeric compositions that may have a relaxation time that corresponds to a single pH value within certain detection ranges. In embodiments, the relaxation time of the polymeric compositions provided herein is unique at each pH within a range of about 4.5 to about 8, about 5 to about 8, about 6 to about 8, about 5 to about 7.5, about 5.5 to about 7.5, about 6 to about 7.5, or about 6.5 to about 7.5.

In one embodiment, the relaxation time of the polymeric compositions provided herein is the transverse relaxation time ($T_2$). In another embodiment, the relaxation time of the polymeric compositions provided herein is the longitudinal relaxation time ($T_1$).

In embodiments, the polymeric compositions provided herein comprise a crosslinked co-polymer comprising a cationic monomer, an anionic monomer, and a crosslinker. The mol ratio of the cationic monomer to the anionic monomer may be about 75:25 to about 25:75, about 70:30 to about 30:70, about 65:35 to about 35:65, about 65:35 to about 55:45, or about 60:40. Not wishing to be bound by any particular theory, it is believed that the mol ratio of the cationic monomer to the anionic monomer can be selected to ensure that each relaxation time of the polymeric compositions provided herein corresponds to a single pH within a preferred detection range of pH values.

As used herein, the phrases "pH sensitive" and "pH sensitivities" generally refer to or describe polymeric compositions or other compositions having relaxation times that are affected by pH. For example, a change of pH may cause a corresponding change of a $T_2$ relaxation time and/or a $T_1$ relaxation time of a polymeric composition or other composition, or, in other words, the $T_2$ relaxation time and/or $T_1$ relaxation time of the polymeric composition or other composition is a function of pH.

Cationic Monomers

The cationic monomer of the polymeric compositions provided herein generally may be any monomer that is capable of forming a biocompatible polymer, and comprises a side chain that includes a moiety that can be positively charged at a certain pH or pH range. Each cationic monomer may include identical side chains, or the cationic monomer may comprise a mixture of two or more monomers, each having a different side chain.

In embodiments, the cationic monomer comprises a side chain that includes a tertiary amine. In one embodiment, the cationic monomer comprises [1] a side chain that includes a tertiary amine, and [2] an acrylate moiety. In another embodiment, the cationic monomer comprises [1] a side chain that includes a tertiary amine, and [2] a methacrylate moiety. In yet another embodiment, the cationic monomer comprises a mixture of cationic monomers comprising a side chain that includes a tertiary amine, wherein a first portion of the cationic monomers includes a methacrylate moiety, and a second portion of the cationic monomers includes an acrylate moiety. Therefore, the cationic monomer can include a mixture of cationic monomers that include different side chains, and/or different polymerizable moieties, such as acrylate or methacrylate moieties.

In embodiments, the cationic monomer comprises a monomer of formula (I):

(I)

wherein $R^1$ is selected from hydrogen or a monovalent $C_1$ hydrocarbyl, $R^2$ is selected from a divalent $C_1$-$C_6$ hydrocarbyl, and $R^3$ and $R^4$ are independently selected from a $C_1$-$C_6$ hydrocarbyl.

Although the monomers herein, such as those of formula (I), are depicted in isolated form for clarity, it is understood by persons of skill in the art that the monomers have a different structure when polymerized and/or crosslinked to form the polymeric compositions provided herein. For example, when a polymeric composition comprises a monomer of formula (I) in its polymeric backbone, the monomer of formula (I) may have the following structure:

(I)

Therefore, the descriptions herein of polymeric compositions comprising the various monomers is not to be construed as implying that the monomers retain the structures herein that depict the monomers in isolated form.

The phrases "$C_1$-$C_6$ hydrocarbyl," "$C_1$-$C_4$ hydrocarbyl," "$C_1$-$C_3$ hydrocarbyl," "$C_2$ hydrocarbyl," "$C_1$ hydrocarbyl," and the like, as used herein, generally refer to aliphatic or aryl groups containing 1 to 6, 1 to 4, 1 to 3, 2, or 1 carbon atoms, respectively. Examples of aliphatic groups, in each instance, include, but are not limited to, an alkyl group, a cycloalkyl group, an alkenyl group, an alkynyl group, an alkadienyl group, a cyclic group, and the like, and includes all substituted, unsubstituted, branched, and linear analogs or derivatives thereof, in each instance having 1 to 6, 1 to 4, 1 to 3, 2, or 1 carbon atoms, etc. Examples of alkyl groups include, but are not limited to, methyl, ethyl, propyl, isopropyl, n-butyl, t-butyl, isobutyl, and pentyl. Cycloalkyl moieties include cyclopropyl, cyclobutyl, cyclopentyl, and cyclohexyl. Additional examples of alkyl moieties have linear and/or branched portions. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, and 3-hexenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, and 5-hexynyl. Examples of aryl moieties include phenyl and any heteroatom substituted derivative thereof, such as pyridinyl.

Unless otherwise indicated, the term "substituted" when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O— alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

In embodiments, the cationic monomer comprises a monomer of formula (I), wherein $R^1$ is a monovalent unsubstituted $C_1$ hydrocarbyl, and $R^2$ is a divalent unsubstituted $C_1$-$C_4$ hydrocarbyl. Therefore, in these embodiments, the cationic monomer is a monomer of formula (IA):

(IA)

In embodiments, the cationic monomer comprises a monomer of formula (IA), wherein each of $R^3$ and $R^4$, independently, is a monovalent unsubstituted $C_1$-$C_3$ hydrocarbyl. Therefore, in these embodiments, the cationic monomer is a monomer of formula (IB):

(IB)

In embodiments, the cationic monomer comprises a monomer of formula (I), wherein $R^1$ is a monovalent unsubstituted $C_1$ hydrocarbyl, $R_2$ is a divalent unsubstituted $C_2$ hydrocarbyl, and $R^3$ and $R^4$ are monovalent unsubstituted $C_1$ hydrocarbyls. Therefore, the cationic monomer, in these embodiments, is 2-(dimethylamino)ethyl methacrylate, which is commonly referred to as dimethylaminoethyl methacrylate (DMAEMA):

(DMAEMA)

In embodiments, the cationic monomer comprises a monomer of formula (I), wherein $R^1$ is hydrogen, and $R^2$ is a divalent unsubstituted $C_1$-$C_4$ hydrocarbyl. Therefore, in these embodiments, the cationic monomer is a monomer of formula (IC):

(IC)

In embodiments, the cationic monomer comprises a monomer of formula (IC), wherein each of $R^3$ and $R^4$, independently, is a monovalent unsubstituted $C_1$-$C_3$ hydrocarbyl. Therefore, in these embodiments, the cationic monomer is a monomer of formula (ID):

(ID)

In embodiments, the cationic monomer comprises a monomer of formula (I), wherein $R^1$ is hydrogen, $R_2$ is a divalent unsubstituted $C_2$ hydrocarbyl, $R^3$ and $R^4$ are monovalent unsubstituted $C_1$ hydrocarbyls. Therefore, the cationic monomer, in these embodiments, is 2-(dimethylamino)ethyl acrylate, which is commonly referred to as dimethylaminoethyl acrylate (DMAEA):

(DMAEMA)

Anionic Monomers

The anionic monomer of the polymeric compositions provided herein generally may be any monomer that is capable of forming a biocompatible polymer, and comprises a side chain that includes a moiety that can be negatively charged at a certain pH or pH range. Each anionic monomer may include identical side chains, or the anionic monomer may comprise a mixture of two or more monomers, each having a different side chain.

In embodiments, the anionic monomer comprises a side chain that includes a carboxylic acid, which may form a carboxylate anion. In one embodiment, the anionic monomer comprises [1] a side chain that includes a carboxylic acid, and [2] an acrylate moiety. In another embodiment, the anionic monomer comprises [1] a side chain that includes a carboxylic acid, and [2] a methacrylate moiety. In yet another embodiment, the anionic monomer comprises a mixture of anionic monomers comprising a side chain that includes a carboxylic acid, wherein a first portion of the anionic monomers includes a methacrylate moiety, and a second portion of the anionic monomers includes an acrylate moiety. Therefore, the anionic monomer can include a mixture of anionic monomers that include different side chains, and/or different polymerizable moieties, such as acrylate or methacrylate moieties.

In embodiments, the anionic monomer comprises a monomer of formula (II):

(II)

wherein $R^5$ is a divalent $C_1$-$C_6$ hydrocarbyl, $R^6$ is selected from hydrogen or a monovalent $C_1$ hydrocarbyl, and m is 0 or 1.

In embodiments, the anionic monomer is a monomer of formula (II), wherein m is 1, $R^6$ is a monovalent unsubstituted $C_1$ hydrocarbyl, i.e., methyl, and $R^5$ is a monovalent unsubstituted $C_1$-$C_3$ hydrocarbyl, and the anionic monomer is a monomer of formula (IIA):

(IIA)

In embodiments, the anionic monomer is a monomer of formula (II), wherein m is 1, $R^6$ is hydrogen, and $R^5$ is a monovalent unsubstituted $C_1$-$C_3$ hydrocarbyl, and the anionic monomer is a monomer of formula (IIB):

(IIB)

In embodiments, the anionic monomer is a monomer of formula (II), wherein m is 0, $R^6$ is hydrogen, and the anionic monomer is acrylic acid.

Crosslinkers

Generally, any crosslinker may be used herein that is capable of reacting with at least one moiety of the cationic monomer, at least one moiety of the anionic monomer, or a combination thereof. The crosslinker may preserve the biocompatibility of the resulting crosslinked polymer.

In embodiments, the crosslinker comprises at least one acrylate moiety. In one embodiment, the crosslinker comprises two acrylate moieties. The crosslinker, therefore, may be a diacrylate crosslinker.

In embodiments, the crosslinker comprises at least one methacrylate moiety. In one embodiment, the crosslinker comprises two methacrylate moieties. The crosslinker, therefore, may be a dimethacrylate crosslinker.

In some embodiments, the crosslinker comprises at least one methacrylate moiety and at least one acrylate moiety. In one embodiment, the crosslinker comprises one acrylate moiety and one methacrylate moiety.

In embodiments, the crosslinker is a diacrylate crosslinker having a structure according to formula (III):

(III)

wherein $R^7$ is a divalent $C_1$-$C_6$ hydrocarbyl.

In one embodiment, the crosslinker has a structure according to formula (III), wherein $R^7$ is a divalent unsubstituted $C_2$ hydrocarbyl, and the dimethacrylate crosslinker is ethylene glycol dimethacrylate (EGDMA).

In embodiments, the crosslinker is a diacrylate crosslinker having a structure according to formula (IV):

(IV)

wherein $R^8$ is a divalent $C_1$-$C_6$ hydrocarbyl.

In one embodiment, the crosslinker is a diacrylate crosslinker having a structure according to formula (IV), wherein $R^8$ is a divalent unsubstituted $C_2$ hydrocarbyl, and the diacrylate crosslinker is ethylene glycol diacrylate.

Generally, the crosslinker may be present in the polymeric compositions provided herein in any amount sufficient to impart one or more desired characteristics to the polymeric compositions.

In embodiments, the crosslinker is present in the polymeric compositions provided herein in an amount of about 0.01 to about 10.0% by weight, based on the total weight of the anionic monomer, the cationic monomer, and the crosslinker. In one embodiment, the crosslinker is present in the polymeric compositions provided herein in an amount of about 0.01 to about 5.0% by weight, based on the total weight of the anionic monomer, the cationic monomer, and the crosslinker. In another embodiment, the crosslinker is present in the polymeric compositions provided herein in an amount of about 1.0 to about 5.0% by weight, based on the total weight of the anionic monomer, the cationic monomer, and the crosslinker. In a further embodiment, the crosslinker is present in the polymeric compositions provided herein in an amount of about 2.0 to about 4.0% by weight, based on the total weight of the anionic monomer, the cationic monomer, and the crosslinker. In a still further embodiment, the crosslinker is present in the polymeric compositions provided herein in an amount of about 2.5 to about 3.5% by weight, based on the total weight of the anionic monomer, the cationic monomer, and the crosslinker. In a particular embodiment, the crosslinker is present in the polymeric compositions provided herein in an amount of about 3.0% by weight, based on the total weight of the anionic monomer, the cationic monomer, and the crosslinker.

In embodiments, the crosslinker is present in the polymeric compositions provided herein in an amount of about 0.01 to about 10.0 mol %, based on the total amount of the cationic and the anionic monomer. In one embodiment, the crosslinker is present in the polymeric compositions provided herein in an amount of about 0.01 to about 5.0 mol %, based on the total amount of the cationic and the anionic monomer. In another embodiment, the crosslinker is present in the polymeric compositions provided herein in an amount of about 1.0 to about 5.0 mol %, based on the total amount of the cationic and anionic monomer. In a further embodiment, the crosslinker is present in the polymeric compositions provided herein in an amount of about 2.0 to about 4.0 mol %, based on the total amount of the cationic and anionic monomer. In a still further embodiment, the crosslinker is present in the polymeric compositions provided herein in an amount of about 2.0 to about 3.0 mol %, based on the total amount of the cationic and anionic monomer. In a particular embodiment, the crosslinker is present in the polymeric compositions provided herein in an amount of about 2.0 mol %, based on the total amount of the cationic and anionic monomer.

Methods of Making Polymeric Compositions

Also provided herein are methods of forming polymeric compositions. The polymeric compositions generally may be formed by contacting an anionic monomer, a cationic monomer, and a crosslinker with an initiator. The components may be contacted in any order. In one embodiment, the cationic monomer, the anionic monomer, and the crosslinker are combined, and then contacted with an initiator. Other processes are possible, however, including contacting the anionic monomer and the cationic monomer with an initiator prior to contacting the monomers with a crosslinker.

In embodiments, the methods comprise providing a mixture comprising an anionic monomer, a cationic monomer, and a crosslinker; contacting the mixture with at least one initiator to form a polymerizable composition; and curing the polymerizable composition to form the polymeric composition.

The mixture comprising the anionic monomer, the cationic monomer, and the crosslinker may be formed by contacting the anionic monomer, the cationic monomer, and the crosslinker in any order. The mixture may further comprise a liquid, such as water. The water may be deionized water.

The mol ratios of the components in the mixture may be selected to facilitate the formation of the polymeric compositions provided herein. For example, the mol ratio of the cationic monomer to the anionic monomer in the mixture may be about 75:25 to about 25:75, about 70:30 to about 30:70, about 55:45 to about 65:35, or about 60:40. The crosslinker may be present in the mixture at a concentration of about 0.01 to about 10% by weight, about 1.0 to about 5.0% by weight, about 2.0 to about 4.0% by weight, about 2.5 to about 3.5% by weight, or about 3.0% by weight, based on the total weight of the anionic monomer, the cationic monomer, and the crosslinker, or, alternatively, the crosslinker may be present in the mixture at a concentration of about 0.01 to about 10 mol %, about 1.0 to about 5.0 mol %, about 2.0 to about 4.0 mol %, about 2.0 to about 3.0 mol %, or about 2.0 mol %, based on the total amount of the cationic monomer and the anionic monomer.

In embodiments, the mol ratio of the cationic monomer to the anionic monomer in the mixture may be about 75:25 to about 25:75, and the crosslinker is present in the mixture at a concentration of about 0.01 to about 5% by weight, based on the total weight of the anionic monomer, the cationic monomer, and the crosslinker, or, alternatively, at a concentration of about 0.01 to about 5 mol %, based on the total amount of the cationic and anionic monomer. In further embodiments, the mol ratio of the cationic monomer to the anionic monomer in the mixture may be about 55:45 to about 65:35, and the crosslinker is present in the mixture at a concentration of about 2.0 to about 4.0% by weight, based on the total weight of the anionic monomer, the cationic monomer, and the crosslinker, or, alternatively about 2.0 to about 4.0 mol %, based on the total amount of the cationic and anionic monomer. In some embodiments, the mol ratio of the cationic monomer to the anionic monomer in the mixture may be about 60:40, and the crosslinker is present in the mixture at a concentration of about 3.0% by weight, based on the total weight of the anionic monomer, the cationic monomer, and the crosslinker, or, alternatively, about 2.0 mol %, based on the total amount of the cationic and anionic monomer.

During and/or after the mixture is formed, the mixture may be placed under vacuum. The mixture may be kept under vacuum for about 1 to about 20 minutes, or longer. The strength of the vacuum may be about 1 to about 6 torr. In one embodiment, the mixture is kept under a vacuum of about 3.5 torr for about 15 minutes.

After the mixture is formed, or after the mixture is formed and placed under vacuum, the mixture may be subjected to one or more thermal treatments. Examples of thermal treatments include [1] a "room temperature (RT) treatment" in which the mixture is maintained at room temperature prior to initiator addition, [2] an "ice treatment" in which the mixture is placed in an ice bath for about 1 to about 20 minutes prior to initiator addition, and [3] a "chilling treatment" in which the mixtures is maintained at 4° C. for about 15 to about 45 minutes prior to initiator addition.

After the mixture or at least a portion thereof has been formed, or after the mixture or at least a portion thereof has been formed and placed under vacuum, or after the mixture or at least a portion thereof has been formed and placed under vacuum and subjected to one or more thermal treatments, an initiator may be added to the mixture to form a polymerizable composition. The initiator may consist of one type of initiator, or the initiator may comprise two or more types of initiators. Generally, the initiator may include one or more compounds capable of facilitating the reaction of one or more of the components in the mixture.

In one embodiment, the initiator comprises ammonium persulfate, tetramethylethylenediamine, or a combination thereof. In another embodiment, the initiator consists of ammonium persulfate. In a further embodiment, the initiator consists of tetramethylethylenediamine. In yet another embodiment, the initiator consists of ammonium persulfate and tetramethylethylenediamine.

The initiator may be added to a liquid prior to its addition to the mixture. In one embodiment, the initiator is added to the mixture as an initiator solution. The initiator solution may have an initiator concentration of about 0.5 mM to about 10 M. The initiator solution may be added dropwise to the mixture.

In one embodiment, the initiator comprises an initiator solution comprising ammonium persulfate, tetramethylethylenediamine, or a combination thereof. In another embodiment, the initiator is an initiator solution comprising ammonium persulfate. In a further embodiment, the initiator includes [1] an initiator solution comprising ammonium persulfate, and [2] neat tetramethylethylenediamine.

The initiator, whether it includes an initiator solution, a neat initiator, or a combination thereof, may be added to the mixture in an amount effective to impart a desired concentration of the initiator in the mixture. For example, the initiator may be an initiator solution comprising ammonium persulfate, and the initiator solution may be added to mixture in an amount effective to impart the mixture with a concentration of ammonium persulfate of about 0.5 mM to about 6 mM, about 1 mM to about 5 mM, about 1 mM, or about 5 mM. As a further example, the initiator may be or include a neat initiator, and the neat initiator may be added to the mixture in an amount effective to impart the mixture with a concentration of the neat initiator, such as tetramethylethylenediamine, of about 0.5 mM to about 6 mM, about 1 mM to about 5 mM, about 1 mM, or about 5 mM.

Not wishing to be bound by any particular theory, it is believed that the average relaxation time (longitudinal or transverse) exhibited by a polymeric composition within a desired pH range can be increased or decreased by varying the types and/or concentrations of initiators, and/or the thermal treatment.

In one embodiment, the at least one initiator comprises tetramethylethylenediamine and a liquid comprising ammonium persulfate, and, after contacting the mixture with the at least one initiator, the concentration of tetramethylethylenediamine in the mixture is about 5 mM, and the concentration of ammonium persulfate in the mixture is about 5 mM; and the polymeric composition has a transverse relaxation time of about 2500 ms to about 2800 ms at a pH of about 7.1 when the transverse relaxation time is measured at a field strength of about 0.5 T.

In one embodiment, the at least one initiator comprises tetramethylethylenediamine and a liquid comprising ammonium persulfate, and, after contacting the mixture with the at least one initiator, the concentration of tetramethylethylenediamine in the mixture is about 5 mM, and the concentration of ammonium persulfate in the mixture is about 5 mM; and the polymeric composition has a transverse relaxation time of about 2400 ms to about 2700 ms at a pH of about 6.7 when the transverse relaxation time is measured at a field strength of about 0.5 T.

In one embodiment, the at least one initiator comprises tetramethylethylenediamine and a liquid comprising ammonium persulfate, and, after contacting the mixture with the at least one initiator, the concentration of tetramethylethylenediamine in the mixture is about 1 mM, and the concentration of ammonium persulfate in the mixture is about 1 mM, and the polymeric composition is made by a process that includes the room temperature thermal treatment.

During and/or after the addition of the initiator, at least a portion of the components of the resulting polymerizable composition may polymerize, crosslink, or a combination thereof.

The polymerizable composition may be cured. The terms "cured," "curing," and the like, as used herein, generally refer to a process that forms a desired polymeric composition by facilitating a desired degree of polymerization and/or crosslinking among the components of a polymerizable composition. In one embodiment, the polymerizable composition is cured at a temperature of about 60° C. to about 120° C. The curing process may last about 10 to about 45 minutes. In a particular embodiment, the polymerizable composition is cured at about 80° C. for about 30 minutes. The polymerizable composition may be cured in a curing vessel capable of imparting a desired shape to the resulting polymeric composition. The polymeric composition also may be sized and/or shaped, for example, by cutting or punching, after curing to impart the polymeric composition with a desired size and/or shape, regardless of the shape of the curing vessel.

Methods of pH Sensing

Methods of pH sensing that rely on the polymeric compositions provided herein also are provided.

In embodiments, the methods of pH sensing comprise providing a polymeric composition as provided herein; associating the polymeric composition with one or more biological tissues, one or more biological liquids, or a combination thereof; measuring a relaxation time of the polymeric composition; and determining a pH of the one or more biological tissues, one or more biological liquids, or a combination thereof. In embodiments, the associating step includes contacting the polymeric composition with the biological tissue or biological liquid in order to determine the pH of the biological liquid or tissue at, or about, the area of contact.

The one or more biological tissues, one or more biological liquids, or a combination thereof may be in vivo or in vitro. In embodiments, associating the polymeric composition with the one or more biological tissues, the one or more biological liquids, or a combination thereof comprises disposing the polymeric composition [1] on at least one surface of the one or more biological tissues, the one or more biological liquids, or a combination thereof, [2] in the one or more biological tissues, the one or more biological liquids, or a combination thereof, or [3] a combination thereof. For example, a polymeric composition may be disposed on one or more surfaces of a tissue, and/or a polymeric composition may be injected into a tissue. In one embodiment, associating the polymeric composition with the one or more biological tissues, the one or more biological liquids, or a combination thereof comprises injecting the polymeric composition into the one or more biological tissues, the one or more biological liquids, or a combination thereof. Not wishing to be bound by any particular theory, it is believed that embodiments of the polymeric compositions provided herein are hydrogels that can be injectable and/or spreadable, and/or can avoid migration upon being associated with one or more biological tissues, one or more biological liquids, or a combination thereof.

Before or after associating the polymeric compositions with one or more biological tissues, one or more biological liquids, or a combination thereof, the polymeric compositions may be allowed adequate time to cure or gel. When the polymeric compositions "cure" or "gel," as those terms are used herein, it means that the one or more functional groups of the anionic monomer, cationic monomer, and/or crosslinker have undergone one or more reactions with each other to a degree sufficient to impart the polymeric composition with one or more desirable characteristics.

The relaxation time of the polymeric compositions may be determined by any means known in the art. In one embodiment, the $T_1$ relaxation time is determined with a magnetic resonance imaging scanner or bench top nuclear magnetic resonance (NMR) system, and an inversion recovery pulse sequence. In another embodiment, the $T_2$ relaxation time is determined with a magnetic resonance imaging scanner or bench top NMR system, and a Car-Purcell-Meiboom-Gill (CPMG) pulse sequence. The relaxation time of the polymeric compositions may be determined in vivo or in vitro. For example, a polymeric composition may be associated with one or more in vivo biological tissues, one or more in vivo biological liquids, or a combination thereof, and the polymeric composition may be analyzed by NMR while associated, or after being associated, with the one or more biological fluids, one or more biological liquids, or a combination thereof. As a further example, a sample of a polymeric composition associated with one or more in vivo biological tissues, one or more in vivo biological liquids, or a combination thereof may be collected and then analyzed by NMR. The collected sample may include at least a portion of the one or more biological tissues, one or more biological liquids, or a combination thereof.

When the relaxation time is determined, it may be compared to a pre-determined standard curve to determine the pH of the one or more biological tissues, one or more biological liquids, or a combination thereof. The pre-determined standard curve may be established by plotting a series of known pH values versus the relaxation times of a polymeric composition at the known pH values. Not wishing to be bound by any particular theory, it is believed that each relaxation time determined for embodiments of the polymeric compositions corresponds to a single physiologically relevant pH, for example, a pH of 4 to 8.5, 4.5 to 8.5, 5.0 to 8.0, 5.5 to 8.0, 5.5 to 7.5, 6.0 to 7.5, or 6.0 to 7.0.

Due to the fact that two or more of the polymeric compositions provided herein may have different pH sensitivities, two or more polymeric compositions may be associated with one or more biological tissues, one or more biological liquids, or a combination thereof, in order to achieve a desired sensitivity within all or part of a particular pH range. The two or more polymeric compositions may be combined with each other before and/or during their association with one or more biological tissues, one or more biological liquids, or a combination thereof. The two or more polymeric compositions may be associated with the one or more biological tissues, one or more biological liquids, or a combination thereof in a separate manner. For example, the two or more polymeric compositions may be disposed on and/or in a two compartment sensor with one compartment housing a first polymeric composition and the second compartment housing a second polymeric composition. As a further example, a first polymeric composition may be associated with one portion of a biological tissue, and a second polymeric composition may be associated with a second portion of the biological tissue. The employment of two or more polymeric compositions can permit the analysis of biological tissues, biological liquids, or a combination thereof that are spatially separated and/or mixed together.

Figure 3:
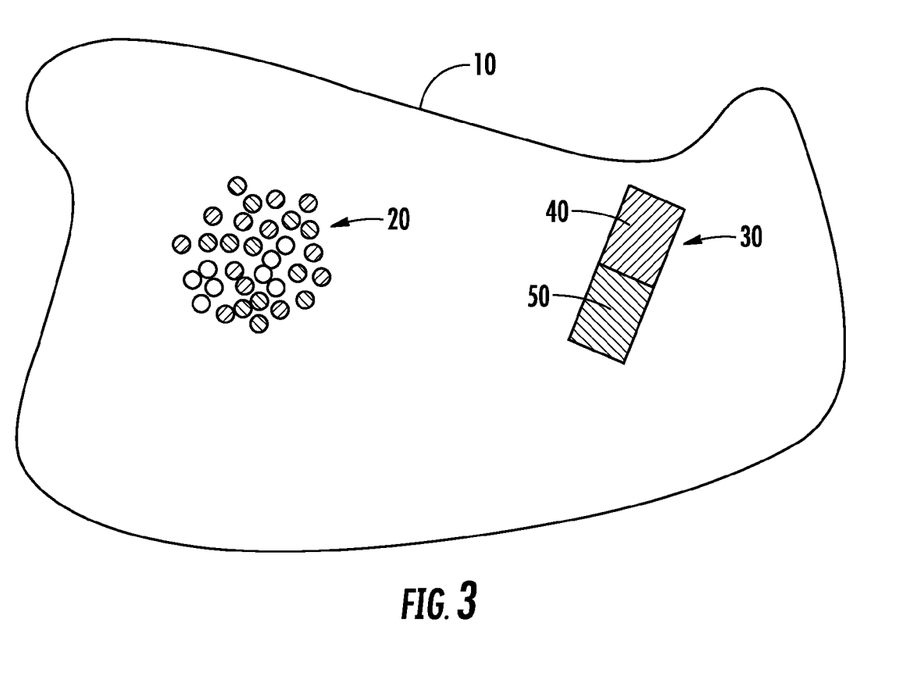
FIG. 3 depicts one embodiment of a two-compartment sensor and one embodiment of a mixture of particles that include a polymeric composition associated with a tissue.

Due to the fact that compositions other than the polymeric compositions provided herein may have different pH sensitivities, one or more of the polymeric compositions provided herein and at least one additional pH sensitive material may be associated with one or more biological tissues, one or more biological liquids, or a combination thereof, in order to achieve a desired sensitivity within all or part of a particular pH range. The one or more polymeric compositions and the at least one additional pH sensitive material may be combined with each other before and/or during their association with one or more biological tissues, one or more biological liquids, or a combination thereof. The one or more polymeric compositions and the at least one additional pH sensitive material may be associated with the one or more biological tissues, one or more biological liquids, or a combination thereof in a separate manner. For example, the one or more polymeric compositions and at least one additional pH sensitive material may be disposed on and/or in a two compartment sensor with one compartment housing a first polymeric composition and the second compartment housing at least one additional pH sensitive material. FIG. 3 depicts one embodiment of two compartment sensor 30 that includes a first compartment 40 that houses a first polymeric composition, and a second compartment 50 that houses at least one additional pH sensitive material. The two compartment sensor 30 is associated with a tissue 10, which may be tumor tissue. As a further example, a first polymeric composition may be associated with one portion of a biological tissue, and at least one additional pH sensitive material may be associated with a second portion of the biological tissue. The employment of one or more polymeric compositions and at least one additional pH sensitive material can permit the analysis of biological tissues, biological liquids, or a combination thereof that are spatially separated and/or mixed together. Examples of the at least one additional pH sensitive material include p-HEMA and p-HEMA-BIS.

Compositions are provided herein that comprise a first polymeric composition, as provided herein, and at least one of [1] a second polymeric composition, as provided herein, and [2] at least one additional pH sensitive material. Therefore, the compositions may include a first polymeric composition, as provided herein, and a second polymeric composition, as provided herein; or a first polymeric composition, as provided herein, and at least one additional pH sensitive material; or a first polymeric composition, as provided herein, a second polymeric composition, as provided herein, and at least one additional pH sensitive material. In embodiments, the first polymeric composition, the second polymeric composition, and the at least one additional pH sensitive material have maximum relaxation times that occur at different pH values. In one embodiment, the first polymeric composition comprises a first crosslinked co-polymer comprising a first cationic monomer, a first anionic monomer, and a first crosslinker; and the first polymeric composition has a relaxation time that is a function of pH; and the second polymeric composition comprises a second crosslinked co-polymer comprising a second cationic monomer, a second anionic monomer, and a second crosslinker, and the second crosslinked co-polymer has a relaxation time that is a function of pH. The relaxation time of the first polymeric composition may be unique at each pH within a range of about 4.5 to about 8, about 5 to about 8, about 6 to about 8, about 5 to about 7.5, about 5.5 to about 7.5, about 6 to about 7.5, or about 6.5 to about 7.5, and the relaxation time of the second polymeric composition may be unique at each pH within a range of about 4.5 to about 8, about 5 to about 8, about 6 to about 8, about 5 to about 7.5, about 5.5 to about 7.5, about 6 to about 7.5, or about 6.5 to about 7.5. The first polymeric composition, the second polymeric composition, and the at least one additional pH sensitive material may be in a particulate form, and the compositions may comprise a mixture of particles. The mixture of particles may be measured in a single voxel, and the relaxation times of the first polymeric composition, the second polymeric composition, and the at least one additional pH sensitive material may be determined with a multi-exponential fitting. FIG. 3 depicts a mixture of particles 20 comprising a first polymeric composition and at least one additional pH sensitive material that is associated with a tissue 10, which may be tumor tissue.

The polymeric compositions provided herein may be associated with any internal or external biological tissues and/or liquids, including human or other mammalian tissues and/or liquids. The biological tissues and/or liquids may be natural or artificially generated, healthy or diseased, such as tumor tissue, or any combination thereof. The biological liquids may be intracellular liquids, extracellular liquids, or any combination thereof. The biological tissues and/or liquids may be in vivo or in vitro. The biological tissues may be skin, bone, ocular, muscular, vascular, an internal organ, such as lung, intestine, heart, liver, etc., or any tumor, and the biological liquids may be blood, bile, lymph fluid, urine, any liquid affiliated with the foregoing biological tissues, or a combination thereof. In one embodiment, the one or more biological tissues comprises tumor tissue. The tumor tissue may include the surface of the tumor, the intratumoral tissue, or a combination thereof.

The methods of pH sensing provided herein may be used as, or as part of, a medical treatment, including cancer treatment. The pH sensing methods provided herein may be used to analyze metastasis, drug resistance, radiotherapy resistance, and/or therapeutic efficiency of cancer treatment. For example, the pH of intratumoral tissue typically decreases if the tumor is receptive to therapy and/or if the therapy has treated the tumor successfully (see, e.g., Lindner, D. et al. "*Intra-tumoural extra-cellular pH: a useful parameter of response to chemotherapy in syngeneic tumour lines*," British Journal of Cancer (2009) 100, 21287-1291). Therefore, the pH sensing methods provided herein may be used to assess therapeutic efficiency, drug resistance, etc. by determining the pH of the intratumoral tissue. The pH sensing methods also may be used to assist the selection of more aggressive cell phenotypes.

Hydrogel Component and Composition Kits

In another aspect, a kit is provided that comprises a polymeric composition and a standard curve. The standard curve may depict a plot of pH versus the relaxation times of the polymeric composition. The standard curve may be included as part of a sheet of instructions, or printed or embossed on any packaging associated with a kit.

In one embodiment, the kits comprise a vial, syringe, or other receptacle that includes the polymeric composition. In another embodiment, the kit comprises two or more vials, each containing a component of the polymeric composition. The two or more vials may be the barrels of a double-barreled syringe. The kit may further include an applicator or other device means, such as a syringe, for storing and/or delivering, via injection and/or topical application, the polymeric composition to one or more biological tissues, one or more biological liquids, or a combination thereof.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Preparation of Polymeric Composition

A polymeric composition was prepared by combining DMAEMA (1.501 g), acrylic acid (AA)(0.461 g), EGDMA (0.063 g), and deionized (DI) water (5.882 g) in a flask, and placing the contents of the flask under vacuum (3.5 torr) for 15 minutes.

Two initiators were then added in an amount of 5 mM each: ammonium persulfate (APS) and tetramethylethylenediamine (TEMED). The flask was then shaken and mixed by inverting the flask three times.

A desired volume of the resulting prepolymer solution was placed in a vessel for curing. The prepolymer solution included the monomers (DMAEMA and acrylic acid), the crosslinker (EGDMA), DI water, and the initiators (APS and TEMED).

The curing vessel was then placed in an oven at 80° C. for 30 minutes. The prepolymer solution was cured into a desired shape, which was imparted by the curing vessel. One sample was cured into a disk-shaped product. Samples of the cured product also were cut into a desired shape, and punched into a desired shape.

Example 2—Preparation of Polymeric Compositions Having Different Ratios of Monomers Using the procedure of Example 1, four polymeric compositions were made having different mol ratios of monomers. The four polymeric compositions had mol ratios of DMAEMA to acrylic acid of 75:25; 70:30; 60:40; and 25:75.

Figure 1:
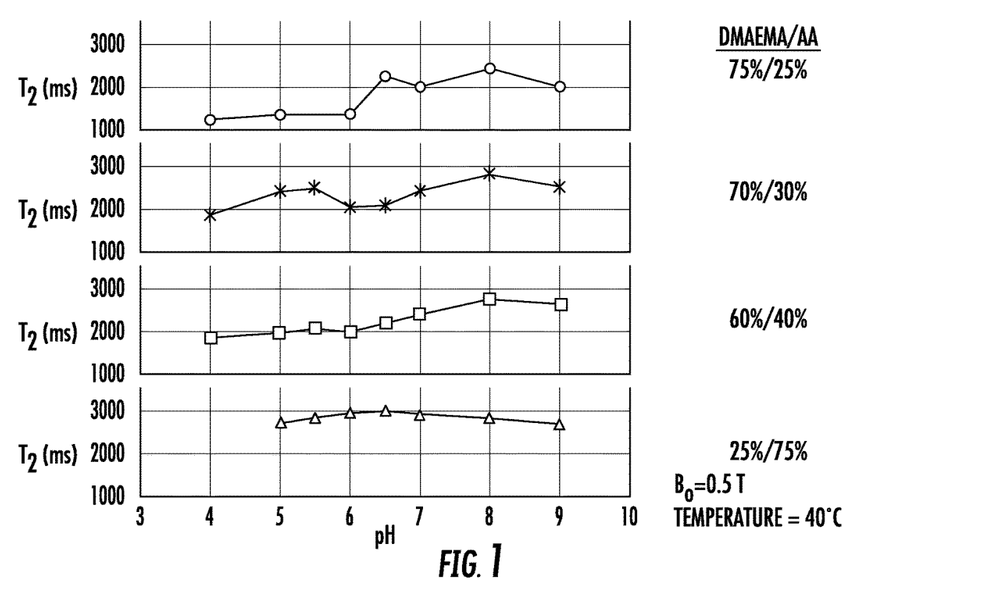
FIG. 1 depicts plots of pH versus $T_2$ relaxation time for several embodiments of polymeric compositions having different ratios of monomers.

At pH values ranging from 4 to 9, the $T_2$ relaxation times of the four polymeric compositions were measured with a bench top NMR system (NMR minispec, Bruker, USA) and a Car-Purcell-Meiboom-Gill (CPMG) pulse sequence. For the measurements of this example, the temperature was 40° C., and $B_0$=0.5 T. The plots of pH versus the $T_2$ relaxation times of the four polymeric compositions are depicted at FIG. 1.

Figure 2:
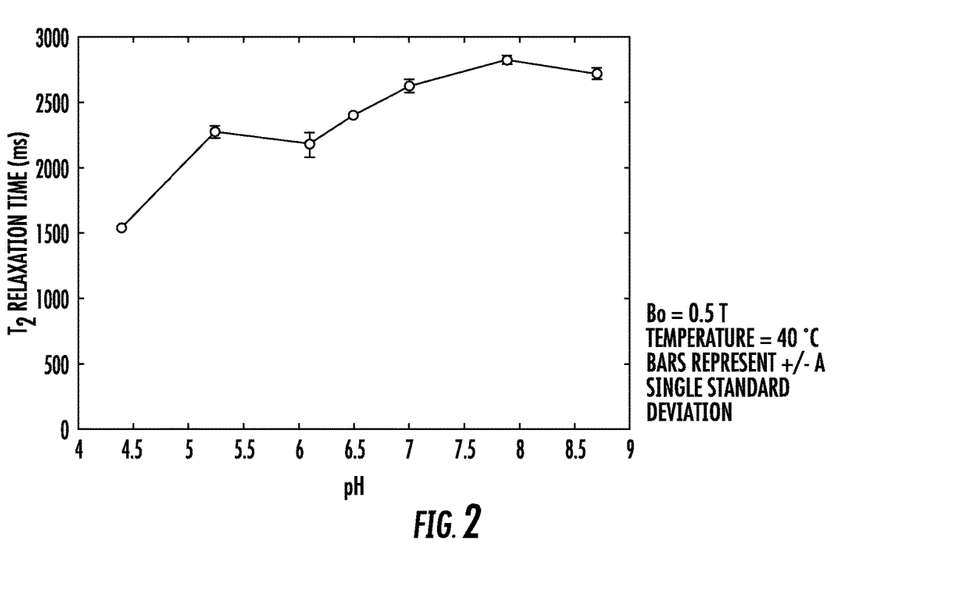
FIG. 2 depicts a plot of pH versus $T_2$ relaxation time for one embodiment of a polymeric composition within one possible range of pH values.

FIG. 2 is a plot of pH values versus the $T_2$ relaxation time of the polymeric composition containing a 60:40 mol ratio of DMAEMA to acrylic acid (temperature=40° C.; $B_0$=0.5 T). The $T_2$ relaxation times of FIG. 2 generally followed as upward trend as the pH increased, especially within the pH range of 6 to 8.

Example 3—Effect of Initiators and Thermal Pre-Treatment

A series of polymeric compositions having a 60:40 mol ratio of DMAEMA to acrylic acid was made with varying [1] types or combinations of initiators, [2] concentrations of initiator(s), and [3] thermal treatments prior to initiator addition.

The series of polymeric compositions of this example were made according to the process of Example 1, except the processes of this example included an additional thermal treatment step that was conducted between removal of the vacuum and the addition of the initiators.

Three thermal treatment steps were tested in this example: [1] a "room temperature (RT) treatment" in which the contents of the flask were maintained at room temperature following mixing and vacuum application until the initiator was added, [2] an "ice treatment" in which the contents of the flask were placed in an ice bath for about 10 minutes prior to initiator addition, and [3] a "chilling treatment" in which the contents of the flask were maintained at 4° C. for 30 minutes prior to initiator addition.

Three initiator configurations also were tested in this example: [1] 5 mM APS and 5 mM TEMED, [2] 1 mM APS and 1 mM TEMED, and [3] 5 mM APS. These final concentrations were achieved by pipetting a concentrated solution of APS or neat TEMED into the mixtures.

The following combinations of the foregoing initiator configurations and thermal treatments were used to make five polymeric compositions:

TABLE 1

Polymeric Compositions Made with Different Initiator Configurations and Thermal Treatments

| Composition No. | Initiator Configuration | Thermal Treatment |
|---|---|---|
| 1 | 5 mM APS and 5 mM TEMED | RT |
| 2 | 1 mM APS and 1 mM TEMED | RT |
| 3 | 5 mM APS and 5 mM TEMED | Ice Treatment |
| 4 | 5 mM APS | RT |
| 5 | 5 mM APS | Chilling Treatment |

Each polymeric composition of Table 1 was made in an 8 mL batch, and 1 mL of each of the polymeric compositions was placed, prior to curing, into six empty NMR tubes having a diameter of about 10 mm.

The $T_2$ relaxation time of the polymeric compositions in each NMR tube was measured and averaged. The difference between the $T_2$ relaxation time of NMR tube 1 and NMR tube 6 also was determined for each polymeric composition. The results of these analyses are depicted in the following table:

TABLE 2

T$_2$ Relaxation Times of Polymeric Compositions Made with Different Initiator Configurations and Thermal Treatments

| Comp. No. | Initiator Configuration | Thermal Treatment | Average T$_2$ Relaxation Time (NMR Tubes 1-6) (ms) | Std. Dev. (NMR Tubes 1-6) (ms) | T$_2$ Relative Time Difference Between NMR Tube 1 and NMR Tube 6 (Tube 1 − Tube 6) |
|---|---|---|---|---|---|
| 1 | 5 mM APS and 5 mM TEMED | RT | 1213 | 120.4 | 322 |
| 2 | 1 mM APS and 1 mM TEMED | RT | 2024 | 30.3 | 82.6 |
| 3 | 5 mM APS and 5 mM TEMED | Ice Treatment | 1191 | 33.4 | −110 |
| 4 | 5 mM APS | RT | 1176 | 35.7 | −114 |
| 5 | 5 mM APS | Chilling Treatment | 1188 | 23.5 | −46 |

The data of Table 2 indicated that altering the types and/or concentrations of initiators, and/or the thermal treatment allowed the average T$_2$ relaxation time and variability (standard deviation and different between tubes 1 and 6) to be controlled.

We claim:

1. A polymeric composition comprising:
   a crosslinked co-polymer comprising a cationic monomer, an anionic monomer, and a crosslinker;
   wherein the mol ratio of the cationic monomer to the anionic monomer is about 60:40,
   the cationic monomer comprises a side chain having a tertiary amine,
   the anionic monomer comprises a side chain having a carboxylic acid,
   the crosslinker comprises at least one of a diacrylate crosslinker and a dimethacrylate crosslinker, and
   the polymeric composition has a relaxation time that is a function of pH.

2. The polymeric composition of claim 1, wherein the relaxation time of the polymeric composition is unique at each pH within a range of about 4.5 to about 8.

3. The polymeric composition of claim 1, wherein the relaxation time of the polymeric composition is unique at each pH within a range of about 6 to about 8.

4. The polymeric composition of claim 1, wherein the relaxation time of the polymeric composition is unique at each pH within a range of about 6 to about 7.5.

5. The polymeric composition of claim 1, wherein the cationic monomer is a monomer of formula (I):

(I)

wherein R$^1$ is selected from hydrogen or a monovalent C$_1$ hydrocarbyl, R$^2$ is selected from a divalent C$_1$-C$_6$ hydrocarbyl, and R$^3$ and R$^4$ are independently selected from a C$_1$-C$_6$ hydrocarbyl.

6. The polymeric composition of claim 5, wherein R$^1$ is a monovalent unsubstituted C$_1$ hydrocarbyl, R$^2$ is a divalent unsubstituted C$_1$-C$_4$ hydrocarbyl, and the cationic monomer is a monomer of formula (IA):

(IA)

7. The polymeric composition of claim 6, wherein each of R$^3$ and R$^4$, independently, is a monovalent unsubstituted C$_1$-C$_3$ hydrocarbyl, and the cationic monomer is a monomer of formula (IB):

(IB)

8. The polymeric composition of claim 5, wherein R$^1$ is a monovalent unsubstituted C$_1$ hydrocarbyl, R$_2$ is a divalent unsubstituted C$_2$ hydrocarbyl, R$^3$ and R$^4$ are monovalent unsubstituted C$_1$ hydrocarbyls, and the cationic monomer is 2-(dimethylamino)ethyl methacrylate.

9. The polymeric composition of claim 1, wherein the anionic monomer is a monomer of formula (II):

(II)

wherein R$^5$ is a divalent C$_1$-C$_6$ hydrocarbyl, R$^6$ is selected from hydrogen or a monovalent C$_1$ hydrocarbyl, and m is 0 or 1.

10. The polymeric composition of claim 9, wherein m is 0, R$^6$ is hydrogen, and the anionic monomer is acrylic acid.

11. The polymeric composition of claim 1, wherein the dimethacrylate crosslinker has a structure according to formula (III):

(III)

wherein R⁷ is a divalent Ci-C6 hydrocarbyl.

12. The polymeric composition of claim 11, wherein $R^7$ is a divalent unsubstituted $C_2$ hydrocarbyl, and the dimethacrylate crosslinker is ethylene glycol dimethacrylate.

13. The polymeric composition of claim 1, wherein the diacrylate crosslinker has a structure according to formula (IV):

(IV)

wherein $R^8$ is a divalent C-$C_6$ hydrocarbyl.

14. The polymeric composition of claim 13, wherein $R^8$ is a divalent unsubstituted $C_2$ hydrocarbyl, and the diacrylate crosslinker is ethylene glycol diacrylate.

15. The polymeric composition of claim 1, wherein the relaxation time is a longitudinal relaxation time.

16. The polymeric composition of claim 1, wherein the relaxation time is a transverse relaxation time.

17. The method of claim 15, wherein curing the polymerizable composition comprises disposing the polymerizable composition in a curing vessel of a desired shape, and heating the polymerizable composition.

18. The method of claim 15, further comprising shaping the polymeric composition.

19. The method of claim 15, wherein the mixture further comprises water.

20. A composition comprising:
  a first polymeric composition comprising a first crosslinked co-polymer comprising a first cationic monomer, a first anionic monomer, and a first crosslinker, wherein the first polymeric composition has a relaxation time that is a function of pH; and
  at least one of a second polymeric composition and at least one additional pH sensitive material.

21. The composition of claim 20, wherein the relaxation time is unique at each pH within a range of about 4.5 to about 8.

22. The composition of claim 20, wherein the relaxation time is unique at each pH within a range of about 6 to about 8.

23. The composition of claim 20, wherein the relaxation time is a longitudinal relaxation time.

24. The composition of claim 20, wherein the relaxation time is a transverse relaxation time.

25. The composition of claim 20, wherein the composition comprises the first polymeric composition and the second polymeric composition, and the first polymeric composition and the second polymeric composition have maximum relaxation times that occur at different pH values.

26. The composition of claim 20, wherein the composition comprises the first polymeric composition and the at least one additional pH sensitive material, and the first polymeric composition and the at least one additional pH sensitive material have maximum relaxation times that occur at different pH values.

27. The composition of claim 20, wherein the second polymeric composition comprises a second crosslinked co-polymer comprising a second cationic monomer, a second anionic monomer, and a second crosslinker; and the second crosslinked co-polymer has a relaxation time that is a function of pH.

28. The composition of claim 20, wherein the relaxation time of the second polymeric composition is unique at each pH within a range of about 4.5 to about 8.

29. The composition of claim 20, wherein the first polymeric composition and the second polymeric composition and/or the at least one additional pH sensitive material are in a particulate form, and the composition comprises a mixture of particles.

30. The composition of claim 29, wherein the mixture of particles is measured in a single voxel, and the relaxation times of the first polymeric composition and the second polymeric composition and/or the at least one additional pH sensitive material are determined with a multi-exponential fitting.

31. The composition of claim 20, wherein the at least one additional pH sensitive material comprises p-HEMA.

32. A sensor comprising the composition of claim 20, wherein the sensor is a two compartment sensor, and the first polymeric composition is disposed on and/or in a first compartment of the sensor, and the second polymeric composition or the at least one additional pH sensitive material is disposed on and/or in a second compartment of the sensor.

* * * * *